(12) United States Patent
Merrill

(10) Patent No.: US 6,232,783 B1
(45) Date of Patent: *May 15, 2001

(54) METHOD FOR MONITORING AN AQUEOUS FLOW USING SELECTIVE FILM

(76) Inventor: John H. Merrill, 3 Adams St., South Portland, ME (US) 04106

( * ) Notice: Subject to any disclaimer, the term of this patent is extended or adjusted under 35 U.S.C. 154(b) by 0 days.

This patent is subject to a terminal disclaimer.

(21) Appl. No.: 09/333,200

(22) Filed: Jun. 15, 1999

Related U.S. Application Data

(63) Continuation-in-part of application No. 08/984,256, filed on Dec. 2, 1997, now Pat. No. 5,990,684.

(51) Int. Cl.[7] .................................................. G01N 27/08
(52) U.S. Cl. ...................... 324/439; 324/71.1; 324/444; 73/61.41; 73/19.1
(58) Field of Search .................................. 324/439, 71.1, 324/444; 340/627; 73/61.41, 19.1

(56) References Cited

U.S. PATENT DOCUMENTS

| | | | |
|---|---|---|---|
| 3,992,662 | * 11/1976 | Koepnick et al. | 324/442 |
| 4,057,481 | * 11/1977 | Lee et al. | 204/296 |
| 4,801,551 | * 1/1989 | Byers et al. | 436/133 |
| 4,871,427 | * 10/1989 | Kolesar, Jr. | 324/443 |
| 5,218,856 | * 6/1993 | Doyle | 73/19.1 |
| 5,282,381 | * 2/1994 | Krone-Schmidt | 73/61.41 |
| 5,990,684 | * 11/1999 | Merrill | 324/439 |

\* cited by examiner

*Primary Examiner*—Glenn W. Brown
*Assistant Examiner*—Wasseem Hamdan
(74) *Attorney, Agent, or Firm*—William B. Ritchie

(57) ABSTRACT

A method and apparatus for detecting contaminants in an aqueous flow. The method includes the steps of providing a conduit having at least one collection portion upon which is disposed a selective film, disposing the aqueous flow through the conduit, attracting contaminants to the collection portion such that they are bonded to the selective film, and detecting a contaminant, or contaminants, based upon a predetermined property of the plurality of contaminants bonded to the ion collection portion. The selective film may include a molecularly imprinted polymer, a crown ether, an antibody selective for biological contaminants, such as Giardia Lamblia and cryptosporidia, or for detecting organics such as dioxin or furan, a cyclodextrin, or a cyclophane. The apparatus includes a conduit having an collection portion with a selective film disposed thereon, a sensor that senses contaminants collected on the collection portion and sends a signal corresponding to a value of a predetermined property of the contaminants, and a microprocessor in communication with the sensor and programmed to process the signal and determine the presence of contaminant based upon the processed signal.

20 Claims, 7 Drawing Sheets

METHOD FOR MONITORING AN AQUEOUS FLOW USING SELECTIVE FILM

This application is a continuation-in-part of U.S. patent application Ser. No. 08/984,256; U.S. Pat. No. 5,990,684, filed on Dec. 2, 1997.

FIELD OF THE INVENTION

The present invention relates to the field of fluid contamination monitors and, in particular, to methods and apparatus for detecting specific contaminants in potable and non-potable water flows using selective film.

BACKGROUND OF THE INVENTION

The Safe Drinking Water Act (SDWA) mandates that municipal water utilities monitor their water. Under the SDWA, the number of monitoring sites in the outgoing distribution system depends upon the number of customers served by the utility. For example, in large utilities serving more than 100,000 customers, the utilities must provide monitoring at 100 sites in the distribution system.

In the drinking water filtration industry, common contaminants of concern are trihalomethanes, biological contamination, nitrate and heavy metals, such as lead. Each are removed by different means within the filtration system. Trihalomethanes are effectively removed with charcoal. Biological contamination such as cysts are removed with fine mesh mechanical filtration. Nitrate and lead are removed by either of two methods, reverse osmosis (RO) or ion exchange resins.

RO systems are effective for removing nitrates and heavy metals. Most quality systems offer a monitor that indicates that there is a rupture in the RO membrane and thus the system requires membrane replacement. Such monitors generally measure the conductivity of the input water and the output water. When the membrane is intact, the conductivity of the input water will differ from that of the output water to the extent that the system is removing inorganic contaminants from the water. When the membrane ruptures, allowing the input water to flow through the membrane, the difference between the conductivity of the input water and the output water will lessen beyond a pre-set threshold and trigger a signal to the user. A disadvantage to RO systems is that they require about five gallons of water to back-flush the membrane for every filtered gallon available for use. For a typical system delivering five gallons of water per day, an RO system will use up to 25 gallons of water per day to back-flush. Thus, while effective for removing inorganic contaminants, RO systems are very wasteful of water.

Ion exchange resins come from the manufacturer in the form of beads, having ion exchange sites on the beads. Cation resins commonly have sodium on the exchange sites and anion resins commonly have chloride ions on the exchange sites. In ion exchange resins, heavier ions displace lighter ions. The following table sets forth a list of cations together with their selectivity coefficients. Selectivity coefficients are indicators of the preference of the resin for each of the ions relative to hydrogen.

TABLE 1

Cation Selectivity Coefficients of Four Cation Resins

| Ion | symbol | selectivity coefficients Cross-linking, wt % | | | |
|---|---|---|---|---|---|
| | | 4 | 8 | 12 | 16 |
| hydrogen | H | 1.0 | 1.0 | 1.0 | 1.0 |
| iron | Fe | 2.4 | 2.55 | 2.7 | 2.9 |
| zinc | Zn | 2.6 | 2.7 | 2.8 | 3.0 |
| cadmium | Cd | 2.8 | 2.95 | 3.3 | 3.95 |
| calcium | Ca | 3.4 | 3.9 | 4.6 | 5.8 |
| strontium | Sr | 3.9 | 4.95 | 6.25 | 8.1 |
| copper | Cu | 3.2 | 5.3 | 9.5 | 14.5 |
| mercury | Hg | 5.1 | 7.2 | 9.7 | 14.0 |
| lead | Pb | 5.4 | 7.5 | 10.1 | 14.5 |

As can be seen from the chart, cations such as iron (Fe), zinc (Zn) and calcium (Ca) have lower preference ratings than mercury (Hg) and lead (Pb). For example, in a cation resin bed having Ca on the exchange sites, if Hg were introduced into the bed, the Hg ions would displace the Ca ions, since Hg is more highly preferred by the ion exchange resin than Ca. If Pb were subsequently introduced, the Pb would displace lighter ions on the resin, and so on.

There are some batch on-line analyzers available on the market that can detect and quantify the presence of contaminants. However, each of these systems is extremely expensive. One system, ChemScan Process Analyzers, available from Applied Spectrometry Associates, Inc. of Waukesha, Wis., uses ultraviolet-visible spectrometry to detect contaminants. This analyzer costs in the $20,000–$40,000 range depending on the contaminants being detected. Ionics, Inc. of Watertown, Mass. offers the OVA 3000 series Trace Chemical Analyzers using the Wet Chemical method for lighter metals and Anodic Stripping Voltammetry for heavier metals. Those systems cost about $40,000. For a large system, having 100 sites, the capital cost of installing such systems would be $4,000,000, which, for a utility serving 100,000 customers, would effect a $40 per customer one time charge for water monitoring. Thus, there is a need for a continuous, on-line system that is economical.

Though water is monitored when it leaves the municipal water plant, some contaminants may get into the water before the water is dispensed from the household tap. One contaminant of special note, lead, is highly toxic. It is present in lead solder in household plumbing, sometimes in the plumbing itself and sometimes in the water's delivery system. Water filtration systems that rely on cation exchange resin technology to remove lead or other toxic heavy metals can work effectively until the ion exchange system is no longer able to capture all of the heavy metals. This point is called the break-through stage. Therefore, it is necessary to detect when the break-through stage is reached. However, the monitor used to detect rupture in an RO membrane will not work in this application as exchange resins saturate gradually with no clearly detectable event such as occurs when an RO membrane ruptures. Thus, there is a need for a monitor to detect the presence of a specific ion, which is a threshold ion in a water filtration system.

Referring to the table, the logical stage to detect cation breakthrough in water from municipal water systems is at the copper level, having the effect of maximizing the longevity of the filtration cartridge and minimizing the health risks. However, an earlier stage threshold ion of cation breakthrough, such as zinc, is preferred for well water users to protect from such harmful ions as cadmium, which would be removed by municipal systems but may be present in wells.

Until recent years, standard anion exchange resins were used to remove nitrate from water. However, sulfates, which are common in nature, had higher selectivity coefficients than nitrate. The result was nitrate sloughing or dumping. That is, if an anion resin column was saturated with nitrate and sulfate was introduced into the column, the sulfates would displace the nitrates, thus, dumping the previously accumulated nitrates into the output water of a filter. Since nitrate has no taste, color or smell, the user was unaware of this event. To correct the problem, ion exchange resin manufacturers developed nitrate selective anion exchange resins which reversed the selectivity coefficients of nitrate and sulfates and thus the problem was solved. However, a disadvantage to using nitrate selective anion resins is that they are about 33% less efficient, i.e., the nitrate selective resins last about a third less long than a conventional anion exchange resin column. Thus, a monitor using nitrate as a target ion would allow the use of the more efficient conventional anion resin, maximize its longevity, and provide an alert to the user that the filter cartridge needed replacement.

In addition to the SDWA, the Clean Water Act (CWA) requires that wastewater treatment plants monitor the influent to their plants for specified contaminants. The CWA also specifies that industrial companies monitor their effluent that feeds into the wastewater stream. Such companies are referred to as Significant Industrial Users or SIU's. These SIU's will typically enter into pre-treatment agreements with their wastewater treatment plants covering the frequency of their monitoring requirement and the contaminants to be monitored.

The following table shows the Maximum Contaminant Levels (MCL's) in parts per million (ppm) of selected inorganic contaminants as mandated by the Environmental Protection Agency (EPA) under the Clean Water Act:

| Contaminant | Symbol | MCL (ppm) |
| --- | --- | --- |
| Copper | Cu | 1.3 |
| Lead | Pb | 0.015 |
| Zinc | Zn | 5.0 |
| Mercury | Hg | 0.002 |
| Arsenic | As | 0.050 |

The frequency of monitoring of wastewater by both the wastewater treatment plants and the SIU's can be annually or more frequently. The common practice for monitoring is to collect water samples in the wastewater stream and submit those samples to testing laboratories for analysis. While the current practice is sufficient to comply with the mandates of the Clean Water Act, there is a possibility that a surge or spike of a contaminant can get into the wastewater treatment plant sludge undetected. Such an event may result in a costly cleanup process and possible fines from the EPA. Thus, there is a need for an in-line, continuous monitor that will detect and quantify contamination spikes in a water flow.

As shown in the Table above, zinc, having an MCL of 5 parts per million is different from mercury, having an MCL of 2 parts per billion. A concentration of 100 parts per billion of mercury would be a spike requiring immediate action. However, a similar reading of 100 parts per billion of zinc would be well within limits and require no action. Therefore, a monitor for heavy metals needs to be sensitive enough to measure vastly differing concentration levels for different contaminants.

As noted above, the USEPA mandates specific MCL's for specific chemicals. However, individual states also have the authority to set their own standards, so long as their standard is at least as stringent as the Federal standard. Thus, monitoring systems must be adjustable to allow the monitoring to be sensitive to differing MCL's in different states.

There is not known in the art a continuous, in-line, contamination monitor for heavy metals that will detect contamination spikes in a water flow, is sensitive enough to measure vastly differing concentration levels for different contaminants, is adjustable to allow the monitoring to be sensitive to differing MCL's in different states, is economical, is not wasteful of water, is capable of detecting when a break-through of a heavy metal filter has occurred, and is capable of providing a user with an alarm to designate when such a filter needs to be replaced.

SUMMARY OF THE INVENTION

The present invention is a method and apparatus for detecting contaminants in an aqueous flow. In its most basic form, the method of the present invention involves providing a conduit having at least one collection portion upon which is disposed a selective film, disposing the aqueous flow through the conduit, attracting contaminants to the collection portion such that they are bonded to the selective film, and detecting a contaminant, or contaminants, based upon a predetermined property of the plurality of contaminants bonded to the ion collection portion. The selective film may include a molecularly imprinted polymer, a crown ether, an antibody selective for biological contaminants, such as Giardia Lamblia and cryptosporidia, or for detecting organics such as dioxin or furan, a cyclodextrin, or a cyclophane.

In its most basic form, the apparatus of the present invention includes a conduit having an collection portion with a selective film disposed thereon, a sensor that senses contaminants collected on the collection portion and sends a signal corresponding to a value of a predetermined property of the contaminants, and a microprocessor in communication with the sensor and programmed to process the signal and determine the presence of contaminant based upon the processed signal. As was the case with the method, the selective film may include a molecularly imprinted polymer, a crown ether, an antibody selective for biological contaminants, such as Giardia Lamblia and cryptosporidia, or for detecting organics such as dioxin or furan, a cyclodextrin, or a cyclophane.

Therefore, it is an aspect of the present invention to provide a water monitoring system that is on-line and continuous.

It is a further aspect of the invention to provide a monitor that is selective for individual contaminants.

Another aspect of the present invention is to provide a monitoring system that can detect and report different concentration levels for different contaminants.

Another aspect of the invention is to provide a monitoring system that is economic to the user.

It is a still further aspect of the invention to provide a monitoring system that may be adapted to monitor organic and inorganic materials.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

The present invention is a monitor apparatus and method of detecting and quantifying specified ions in an aqueous flow. In its most basic form, the monitor of the present invention involves the doping of a target ion onto an ion exchange resin and measuring the presence of this target ion in the flow of analyte downstream of the resin.

Figure 1A:
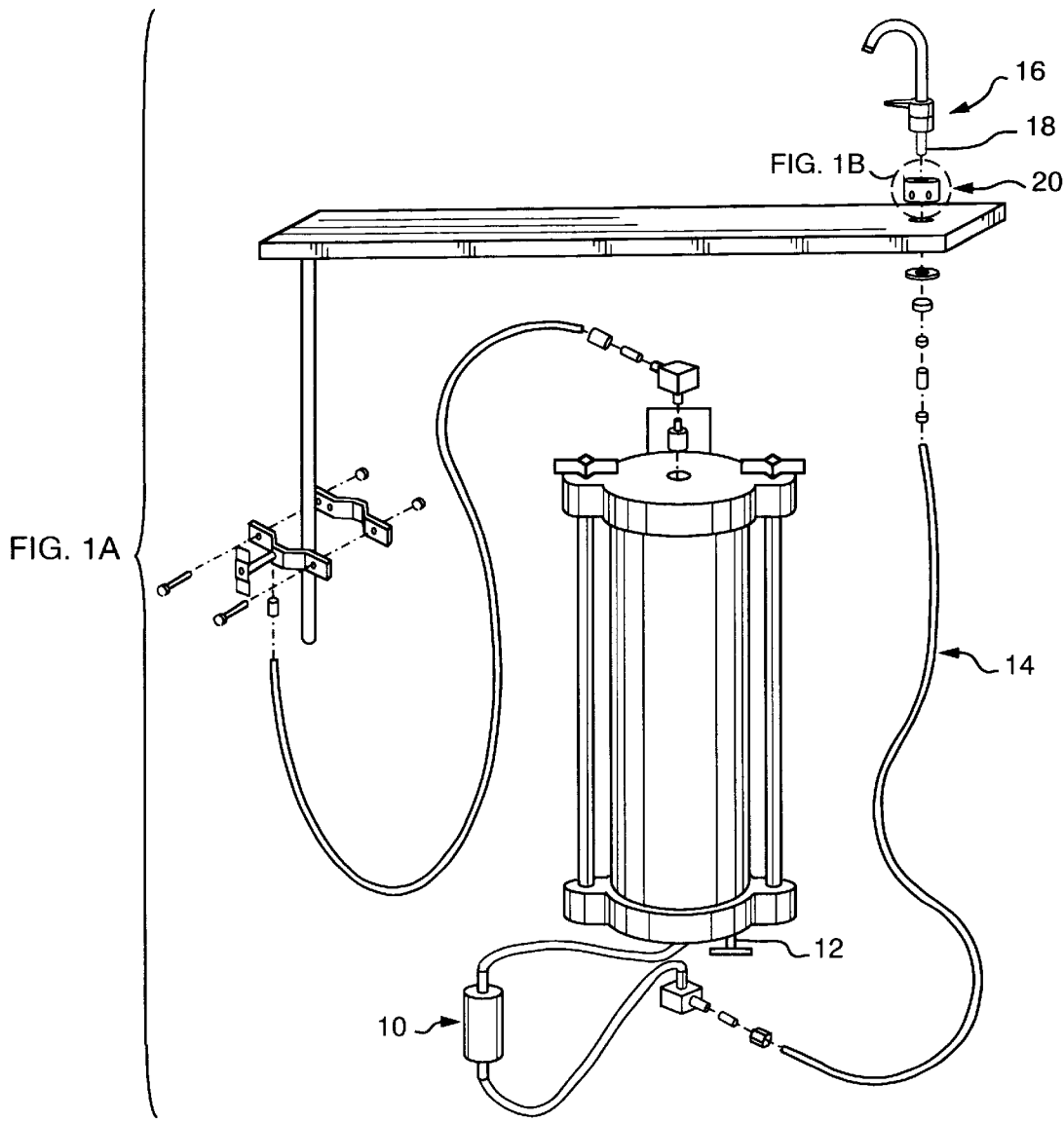
FIG. 1 is an isometric view of a home water filtration system employing one embodiment of the monitor of the present invention.
Figure 1B:
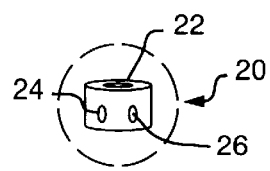
Figure 2:
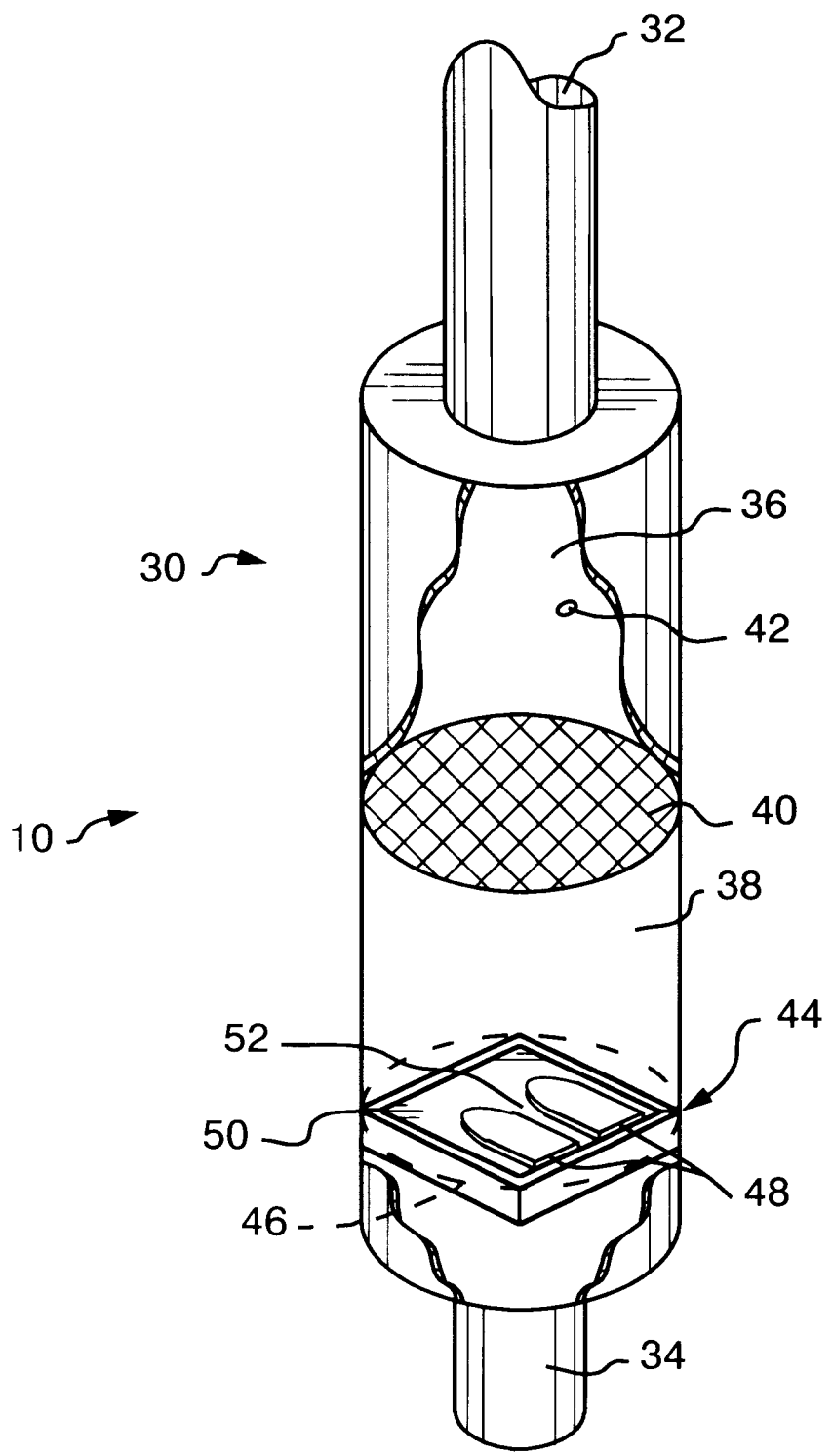
FIG. 2 is an isometric section view of the preferred embodiment of the monitor of FIG. 1.

Referring now to FIGS. 1 and 2, the preferred embodiment of the present invention, utilizing ion detection techniques as a monitor to detect failure of a water filter, is disclosed. As shown in FIG. 1, a monitor 10 is located at an outlet end 12 of a water filter system 14 having a conduit in which an ion exchange resin (not shown) is disposed. The water filtration system 14 has a water-dispensing faucet 16, which has a threaded male connector 18. A faucet collar 20 is located under the dispensing faucet 16 with the threaded male connector 18 extending through a faucet engaging hole 22 of the faucet collar 20. The faucet collar 20 has a green light 24 and a red light 26. The green light 24 is illuminated when water is dispensed from the faucet 16 until the monitor 10 detects the presence of a target ion T, at which time the red light 26 is illuminated on the faucet collar 20.

As shown in FIG. 2, the monitor 10 has a conduit 30. The conduit 30 has an inlet 32, an outlet 34, and a top region 36 and a bottom region 38 separated by a restraining screen 40. An ion exchange resin bed 42, doped with a target ion T, is contained in the top region 36 of the conduit 30. A sensor substrate 44 is positioned in the bottom region 38 of the conduit 30. The sensor substrate 44 has an insulator layer 46, conductive pads 48 and a polymer layer 50 which is selective for the target ion, T. The conductive pads 48 are connected to a constant current supply (not shown) and, in the preferred embodiment, are gold. However, other conductive materials commonly used in such applications may be used to achieve similar results.

Analyte water exiting the water filter 14 enters the monitor inlet 32 and passes into the ion exchange resin bed 42. Ions in the analyte having a selectivity coefficient higher than the target ion, T, will displace the target ion, while ions having selectivity coefficients lower than, T, will not displace target ions in the ion exchange resin bed 42. The analyte water passing from the ion exchange resin bed 42 passes across the polymer layer 50 of the sensor substrate 44. Any target ions in the analyte will affix to the polymer layer 50 in a conductive bridge 52 between the conductive pads 48, changing the voltage of the current flow in the constant current source. Ohm's Law states that:

$$I=E/R,$$

where:

I is the electrical current measured in amperes, and

E is the electromotive force expressed in volts, and R is the resistance, expressed in ohms, $\Omega$.

When the target ions, T, cause a change in conductivity between the conductive pads 48, the resultant change to the resistance, R, in the equation, necessitates a corresponding change in E to maintain a constant current I. The change in voltage is detected by a voltmeter. When the voltage change differs from a pre-set threshold level, the green light 24 on the faucet collar 20 is disabled and the red light 26 is enabled, effectively signaling the user that it is time to change the water filter cartridge.

The foregoing embodiment has been described in terms of the 8% cross-linked ion exchange resin set forth in Table 1, with the target ion being copper. In that embodiment, if either mercury, Hg or lead, Pb were present in the influent, they would displace the Cu ions on the ion exchange resin column and trigger the sensor. Table 1 sets forth another Purolite cation resin, a 4% cross-linked resin which has different selectivity coefficients from the 8% cross-linked resin.

In the 4% resin, the ions with higher selectivity coefficients than Cu are Ca, Sr, Hg and Pb. Thus, Ca and Sr are higher than Cu in the 4% resin and lower than Cu in the 8% resin. Thus, by employing the 4% resin in the monitor, the signal means would be triggered by the presence of Ca and Sr, whereas by employing the 8% resin, the signal means would not be triggered by the presence of either Ca or Sr. Thus, the present invention allows for selection of ions to be detected, based on the selection of the ion exchange resin selected for the ion exchange column.

In another embodiment of the present invention, two or more monitors are situated in parallel. Using the example in the preceding paragraph, if the monitor was employed to determine the presence of Ca or Sr in a water stream, one monitor would employ the 8% resin and the other would employ the 4% with Cu being the target ion. If neither monitor triggered the signal means, then the water stream would not be at a breakthrough state for Ca or Sr, for in this example, either Ca or Sr would trigger monitor 2. If monitor 2 was triggered but monitor 1 was not triggered, then the water stream must contain Ca or Sr, for if any other ions triggered monitor 2, then monitor 1 would be triggered also. Thus, by employing more than one monitor, each with different ion exchange resins in the resin column, the monitor of the present invention can isolate specific ions or groups of ions.

In one embodiment of the invention, the monitor employs reference ions, target ions and marker ions. The reference ions are ions having a selectivity coefficient immediately higher than the target ion on a chart of ion exchange resin selectivity coefficients. The target ions are the ions being detected and quantified. The marker ions are ions having a selectivity coefficient immediately lower than the target ion. Selectivity coefficients are measures of the attraction of an ion to an ion exchange resin. For cations, the coefficients are expressed as the attraction relative to hydrogen. For anions, the coefficients are expressed as the attraction relative to hydroxide.

To detect and quantify a first target ion, the monitor has a first sensor which, with calculations in a microprocessor, determines the number of first reference ions in the analyte. A second sensor, which employs first marker ions, and with calculations in the microprocessor, determines the total number of first target ions in the analyte. The monitor has a flow meter, which provides flow rate of the analyte. The microprocessor computes the concentration of the first target ions in the analyte, adjusted by the capture ratio of the ion exchange resin, by dividing the number of first target ions in the analyte by the flow rate of the analyte.

A third sensor is employed to detect and quantify a second target ion. The first target ion which was detected and quantified in the second sensor, becomes a second reference ion for the second target ion detected in the third sensor and the first marker ion used in the second sensor becomes the second target ion detected in the third sensor.

The number of different target ions that can be detected and quantified by a single monitor of the present invention is limited only by the availability of ion exchange resins to differentiate among ions. The monitor requires an ion having a selectivity coefficient immediately higher and immediately lower than the target ion. The detected ions can be cations or anions.

It is preferred that adjoining cations have the maximum separation in their selectivity coefficients. Thus, referring to Table 1, in a sensor with copper as a target ion, strontium is an adjoining ion, having the next lower selectivity coefficient, for both the 8% and 12% cross-linked resins. The preferred choice of resin is the 12%, because the separation (9.5−6.25=2.25) is greater than the 8% resin (5.3−4.95=0.35).

The monitor may be connected to a microprocessor and has a base unit comprising a base unit water inlet, a base unit water outlet and sensor cartridges. The sensor cartridges each have a water inlet, a sensor and a water outlet. In some embodiments, the sensors have a layer of ion exchange resin and a bulk acoustic wave (BAW) device to detect changes in mass in the ion exchange resin layer and an insulator. In these embodiments, the layer of resin is deposited on the bulk acoustic wave (BAW) device or a substrate in vibratory contact with the BAW device.

The BAW device consists of a thin, flat piezoelectric crystal having metal electrodes covering the top and bottom faces. Piezoelectric crystals are well known in the art and have been applied to a number of applications, including a variety of sensor applications. Since the BAW substrate is piezoelectric in nature, an applied potential results in a corresponding mechanical deformation. Furthermore, due to its elasticity, the substrate "springs" back to its original shape upon removal of this potential. Because of the finite inertia of the crystal, however, the crystal behaves as a mass on a spring, oscillating at a characteristic frequency for some time until the acoustic wave is finally damped out. Such a situation is analogous to a guitar string, oscillating at a specific pitch after it has been plucked. In this particular case, however, since the substrate is piezoelectric in nature, a corresponding electrical signal appears on the metal electrodes of the device. By amplifying this electrical signal and feeding it back to the crystal, an extremely stable oscillator can be realized. This oscillation frequency is almost exactly the resonant frequency of the BAW device, differing only enough to account for any electrical phase shift through the amplifier. The resonant frequency of the BAW device, however, is highly dependent upon a number of parameters, including the velocity, v, at which the wave travels through the bulk of the crystal, the thickness, t, of the crystal, and the interaction of the BAW with the surfaces of the device (i.e., the boundary conditions). To a first approximation, the first two parameters, v and t, remain constant. Upon application of any thin film to the surface of the device, however, the resonant frequency becomes highly dependent upon the elastic properties of the film, the electrical conductivity of the film, and the mass of the film. Thus, a BAW crystal oscillator can be utilized as a very sensitive microbalance for the measurement of masses in the nanogram range.

As a thin film of matter collects on the surface of the crystal, the change in mass is manifested as a change in BAW resonant frequency, which is, in turn, manifested as a change in the oscillation frequency. This frequency change can be modeled by Sauerbrey's equation, as follows, $$m \approx \frac{(\Delta f) v_s \rho_s A}{2(f_0)^2}$$

where m is the mass loaded onto the device (in kg), $f_0$ is the nominal resonant frequency of the device (in Hz), $\Delta f$ is the change in frequency (in Hz), $v_s$ is the velocity of the BAW in the substrate (in m/s), $\rho_s$ is the density of the substrate (in kg/m$^3$), and A is the active surface area of the device (in cm$^2$). While this equation neglects film elasticity and conductivity, it provides an excellent model for frequency changes due to mass loading of the device. For a 15 MHz AT-cut quartz crystal, the minimum detectable frequency change (1 Hz) corresponds to a change in mass of about 2 nanograms/cm$^2$.

The mass change of an applied film on the BAW device will have a similar effect on the frequency of the device as described above for the deposition of a film on a bare device. Thus, in the present invention, a first metal electrode is coated with a layer of ion exchange resin, preferably of a thickness of about one micron. The layer is subsequently doped with the target ion, T, the reference ion, R or the marker ion, M.

In a monitor base unit configured to detect and quantify a target ion, the base unit has a container of ion exchange resin, doped with a reference ion, R, with R having selectivity coefficient immediately higher than a first target ion, T, a first sensor cartridge and a second sensor cartridge. The first sensor cartridge has a first sensor. The second sensor cartridge has a second sensor. The first sensor has a layer of ion exchange resin incorporated on a top electrode of a first BAW device doped with the target ion, T. A second ion exchange resin layer incorporated on a second electrode of the second sensor is doped with a marker ion, M, the ion having the next lower selectivity coefficient in the ion exchange resin table from the target ion, T.

The analyte passes from a monitor base unit water inlet into the container of ion exchange resin. All ions in the analyte having selectivity coefficients higher than the reference ion, R, will affix to the ion exchange resin and exchange for the reference ion, R. Thus, the output water from the container may contain R, or ions having selectivity coefficients less than R, including the target ion, T. The water, exiting the container, passes into the first sensor cartridge, having the first sensor with a layer of ion exchange resin doped with the target ion, T.

The reference ions R, in the water will affix to the layer and exchange with target ions, T, on the layer. Any target ions, T, in the water will either displace the target ion, T, on the first layer or they will pass by the first layer without displacing any target ions. In either case, the net effect to the mass of the layer will be zero. Ions having lower selectivity coefficients will not displace target ions, T, on the first layer. Thus, the water, having passed the first sensor, will contain either target ions extant in the analyte, the displaced target ions, or ions having selectivity coefficients lower than the target ions. The exchange of reference ions, R, on the first layer will increase the mass of the first layer to the extent that reference ions, R, are present in the water, less the mass of the target ions, T, displaced by the reference ions, R.

In operation, the water passes from the container into the first sensor cartridge and passes over the first layer of ion exchange resin incorporated on the top electrode of the BAW device. In this embodiment, it is preferred that a bed of ion exchange resin be downstream from each sensor, with the resin being doped with the same ion as the doped ion on the preceding sensor. When the output water from the first sensor passes by the second layer on the second sensor doped with the marker ions, M, the target ions, T, in the water will exchange with the marker ions, M. residing on the layer.

The exchange of target ions, T, on the second ion exchange resin layer will increase the mass of the second layer, less the mass of the marker ions, M, displaced to the extent that target ions, T, are present in the water. The mass change, $m_1$, of the first sensor, will be the mass of the reference ions, R, less the target ions, T, displaced and can be expressed as follows:

$$m_1 = R_A W_R - R_A W_T$$

where:

$R_A$ is the number of reference ions $W_R$ is the atomic weight of the reference ions and $W_T$ is the atomic weight of the target ions.

Thus, the number of reference ions, $R_A$ is expressed as:

$$R_A = \frac{m_1}{(W_R - W_T)}$$

The mass change, $m_2$, on the second sensor, will be the mass of the target ions displaced by the reference ions, R, plus the mass of the target ions, T, in the analyte less the weight of the marker ions, M, displaced by the target ions, M, and can be expressed as follows:

$$m_2 = R_A W_T + T_A W_T - (R_A + T_A) W_M$$

where:

$T_A$ is the number of target ions in the analyte and $W_M$ is the atomic weight of the marker ions.

Thus, the number of target ions in the analyte is expressed as follows:

$$T_A = \frac{m_2 - R_A(W_T - W_M)}{(W_T - W_M)}$$

The increase in mass on the second layer will result in a decrease in the frequency of the BAW device measured in MHz. The frequency decrease is recorded by the microprocessor in one-second intervals. The decreased frequency is converted to $m_2$, the mass change on the second sensor layer during the interval. Simultaneously, the microprocessor accepts input from a flow meter, recording the passing of water into the monitor base unit in ml/sec. The microprocessor will convert the change in frequency to the number of atoms per second, adjust the number of atoms by the capture ratio of the ion exchange resin and divide by the ml/sec recorded from the flow meter. The result is a reading of the presence of the target ion, T. Since the BAW records the mass changes in the sub-pictogram to microgram range, the resultant measurement will be in parts-per-billion (ppb).

For the detection and quantification of a second target ion, T', the monitor base unit has a third cartridge having a third sensor with a third layer doped with a marker ion, M'. In order to quantify the second ion, T', the value for the number of target ions, T, becomes $R_A$, the number of reference ions, R', in the calculation required to quantify the second target ion, T'. The marker ion, M, on the second layer of the second sensor becomes the target ion, T', for detection of the second target ion, T'. Thus, the computation for the second target ion, T', is as follows:

$$m_3 = R'_A W_{T'} + T'_A W_{T'} - (R'_A + T'_A) W_{M'}$$

where:

$R'_A$ is $T_A$, the number of target ions, T.

$T'_A$ is the number of target ions in the analyte, and $W_{M'}$ is the atomic weight of the marker ions, M'.

Thus, the number of target ions in the analyte is expressed as follows:

$$T'_A = \frac{m_3 - R'_A(W_{T'} - W_{M'})}{(W_{T'} - W_{M'})}$$

As is apparent from the above description, monitors of the present invention may be employed to detect and quantify multiple ions. For example, a monitor may be configured to detect mercury and copper. In such a monitor, the container of ion exchange resin is doped with lead. The analyte passes into the container and the ions heavier than lead exchange with the lead. The analyte passes over the first sensor layer which has an ion exchange resin doped with mercury. The lead exchanges with the mercury. The water passes through a resin bed doped with mercury to capture any lead ions that failed to exchange with the mercury on the first sensor layer. Thus the water now has the mercury that was displaced, the mercury in the analyte and cations lighter than mercury. The water passes over the second sensor, which is doped with copper. The mercury, and only the mercury, exchanges with the copper. The layer of the third sensor is doped with calcium. The copper from the second sensor displaces the calcium ions on the third sensor, and so on.

The weight change on the first sensor layer is the weight of lead less the weight of the mercury displaced by the lead. Since the unit weight of the lead and mercury are known, the number of lead ions is calculated. The exchange of mercury with lead is a one-for-one exchange. Thus, the number of mercury ions displaced is known. The weight change on the second layer is (1) the weight of the mercury which was displaced by the lead, (2) the weight of the mercury in the analyte and (3) less the weight of the copper ions displaced. The unit weights of mercury and copper are known and, thus, the total weight of the mercury, and the total number of mercury ions, on the layer is known. Subtracting the number of displaced mercury ions from the total mercury ions on the layer yields the number of mercury ions in the analyte. The calculations for the copper detection are the same as that for mercury.

It should be appreciated that the monitor will detect and quantify multiple ions so long as the ions being detected have ions with adjacent selectivity coefficients. If there is a break in the succession for selectivity, the sensor cartridge for the ion having the highest selectivity in a contiguous group must be preceded with a container of ion exchange resin having the next higher selectivity coefficient on the exchange sites of the resin.

Figure 3:
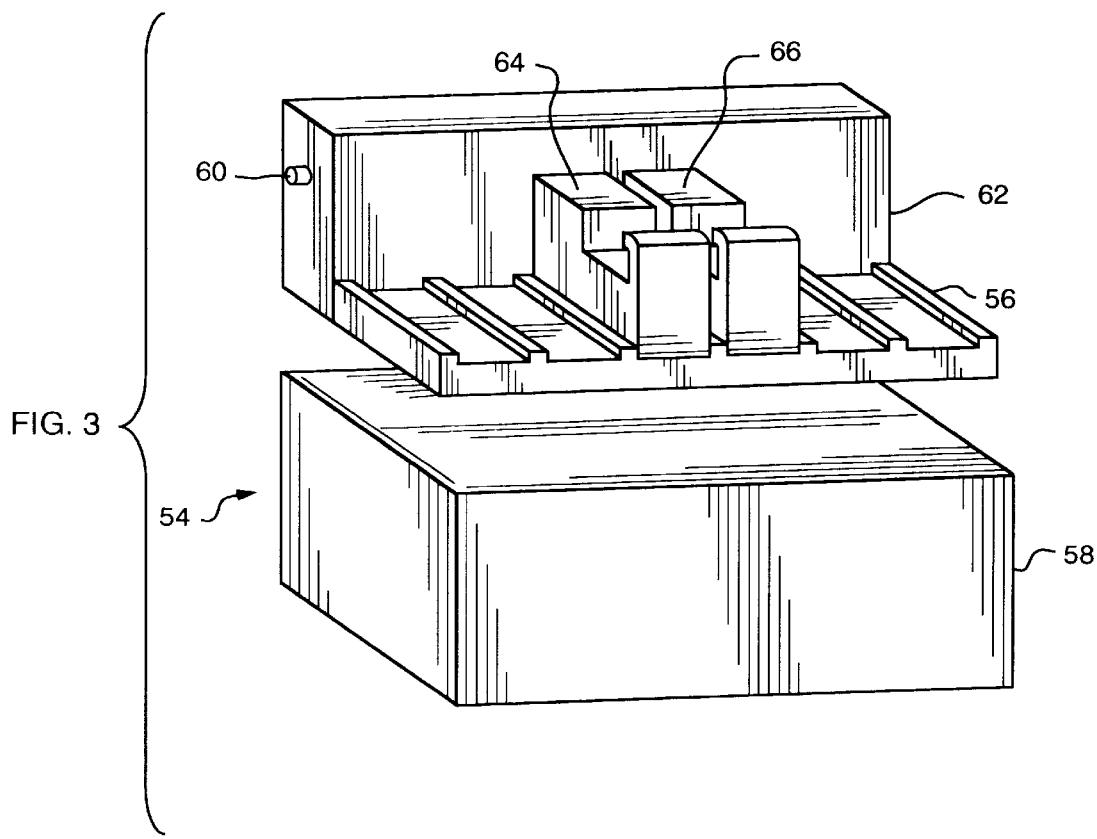
FIG. 3 is an isometric view of a monitor having a monitor base unit connected to a microprocessor and having two sensor cartridges.

Referring now to FIG. 3, one embodiment of the apparatus of the present invention, adapted to monitor two ions, is shown. The monitor 54 has a monitor base unit 56, connected to a microprocessor 58. The monitor base unit 56 has a base unit water inlet 60, a base unit water outlet 62, a first sensor cartridge 64, and a second sensor cartridge 66.

Figure 4:
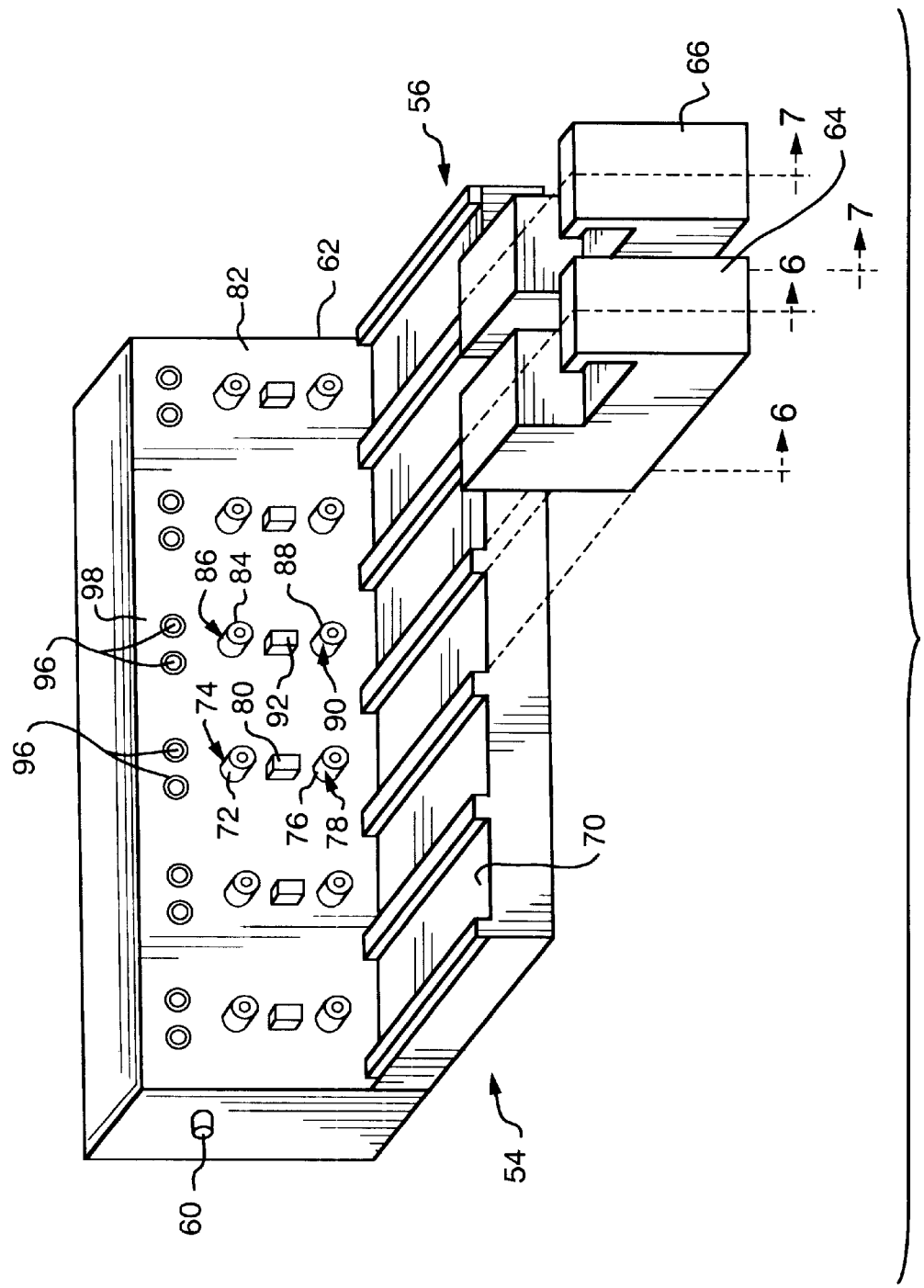
FIG. 4 is an isometric view of the monitor base unit showing sensor cartridge engaging slots and the water and electrical connectors.

As viewed in FIG. 4, the sensor cartridges 64 and 66 engage cartridge engaging slots 70 when seated on the monitor base unit 56. When seated, the first sensor cartridge, 64 engages a first water inlet nipple 72 located in a first water inlet 74, a first water outlet nipple 76, located in a first water outlet 78 and a pair of electrical connector pins 80 located on a rear surface 82 of the monitor base unit 56. The second sensor cartridge 66 engages a second water inlet nipple 84 located in a second water inlet 86, a second water outlet nipple 88, located in a second water outlet 90 and a pair of electrical connector pins 92 located on the rear surface 82 of the monitor base unit 56. The water inlet nipples and water outlet nipples 72, 76, 84, 88 have circumferentially mounted O-rings 94 located in O-ring grooves 95 (shown in FIG. 6). Pairs of indicator lights 96, are located in a top region 98 of the rear surface 82 for each sensor cartridge 64 and 66. The pairs of indicator lights, 96 flash green when the sensor cartridges 64 and 66 are operational and flash red when the sensor cartridges 64 and 66 need replacement.

Figure 5:
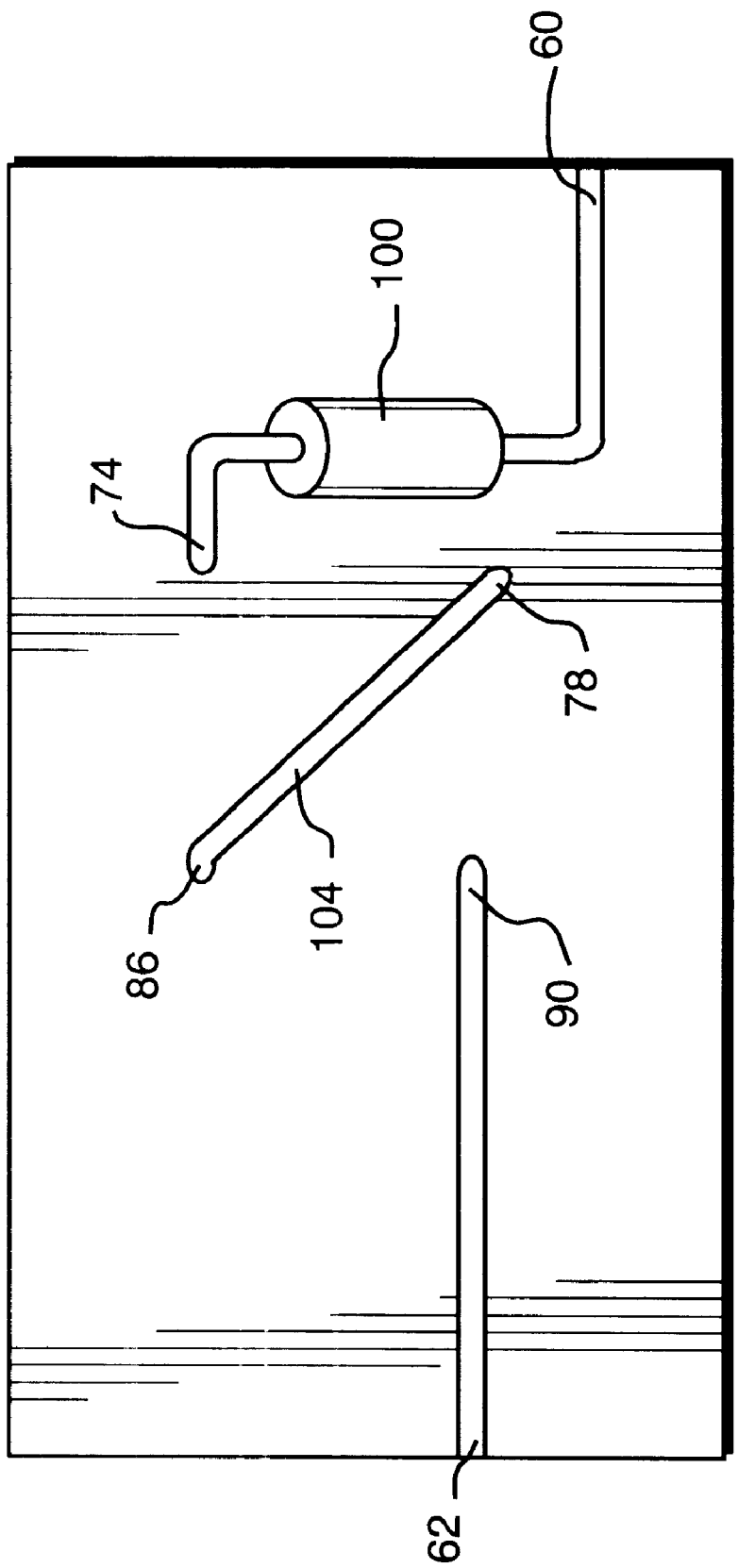
FIG. 5 is a rear elevation view of the monitor base unit showing a container of doped ion exchange resins and the water connections between two sensor cartridges.

As viewed in FIG. 5, the analyte water enters the base unit water inlet 60, passes into a container 100, which contains a bed of ion exchange resin doped with the reference ion, R, where the ions heavier than the reference ion exchange for the reference ion. The water exiting the container 100 passes into the first water inlet 74. Water exiting the first sensor cartridge 64 passes through the first water outlet 78, and flows through a tube 104 into the second water inlet 86. Water exiting the second sensor cartridge 66 passes through the second water outlet 90 and on through the base unit water outlet 62.

Figure 6:
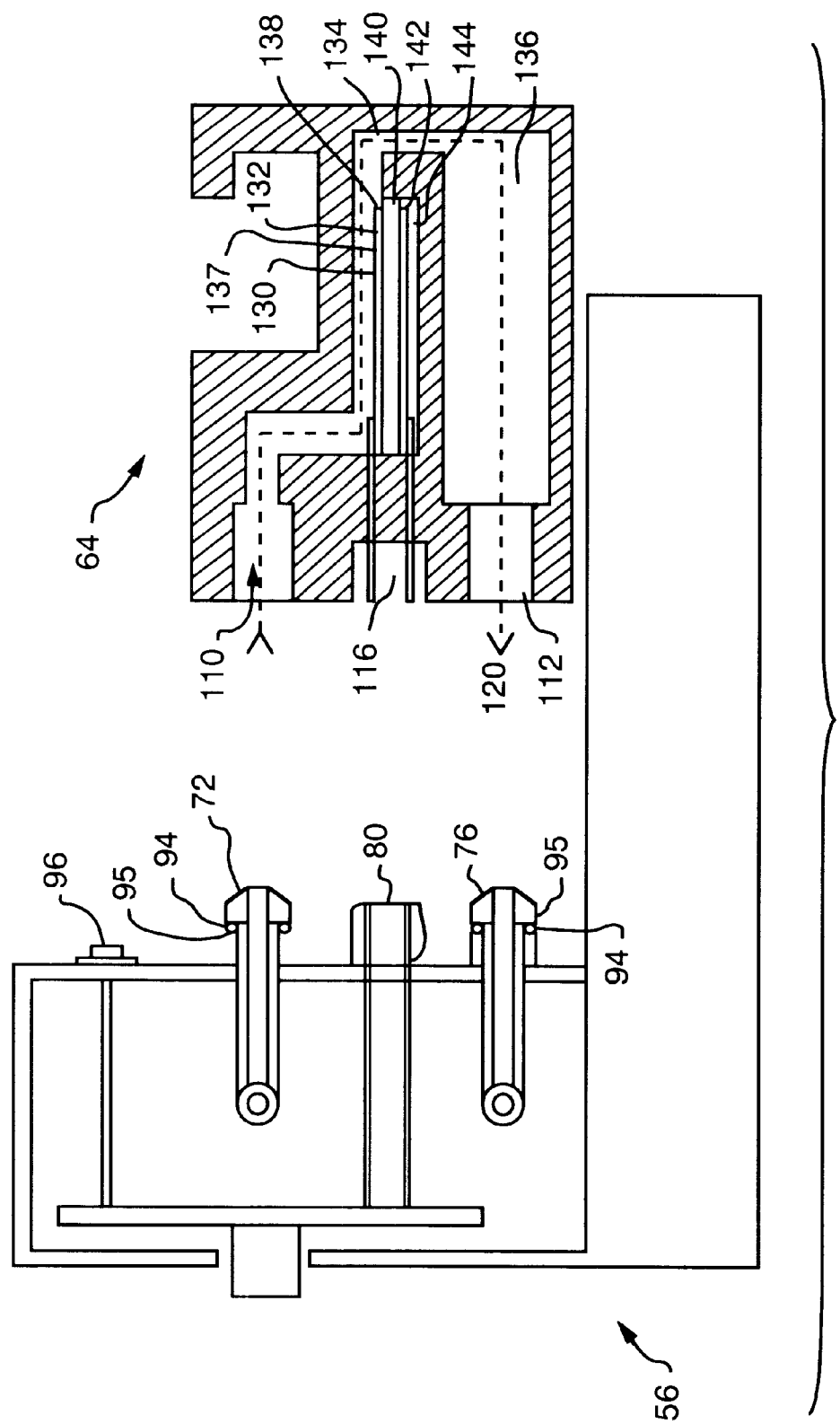
FIG. 6 is a cut side view of a first sensor cartridge, showing a water inlet and outlet and a resin incorporated BAW device.

FIG. 6 shows the first sensor cartridge 64. When in its seated position, as shown in FIG. 3, the first water inlet nipple 72 engages a water inlet recess 110, the first water outlet nipple 76 engages a water outlet recess 112 and the electrical connector pins 80 engage an electrical pin recess 116.

The analyte water, shown in a flow path 120, enters the first sensor cartridge 64 through the water inlet recess 110, passes across a top surface 130 of a first BAW device 132, passes a water exit passage 134, and flows through a first bed of ion resin exchange resin 136. The first BAW device, 132, has a layer of ion exchange resin 137 doped with a target ion, T, a top electrode 138, a layer of piezoelectric crystal 140, a bottom electrode 142 and an insulator 144. Though quartz crystals, such as those commercially available from Sawtek, Inc., Orlando, Fla. and Motorola, Inc. Phoenix, Ariz., are the preferred piezoelectric crystals, other crystals exhibiting piezoelectric properties may also be used to achieve similar results. It is also preferred that the insulator 144 encapsulate the bottom electrode 142 to isolate the bottom electrode 142 from the analyte water.

Figure 7:
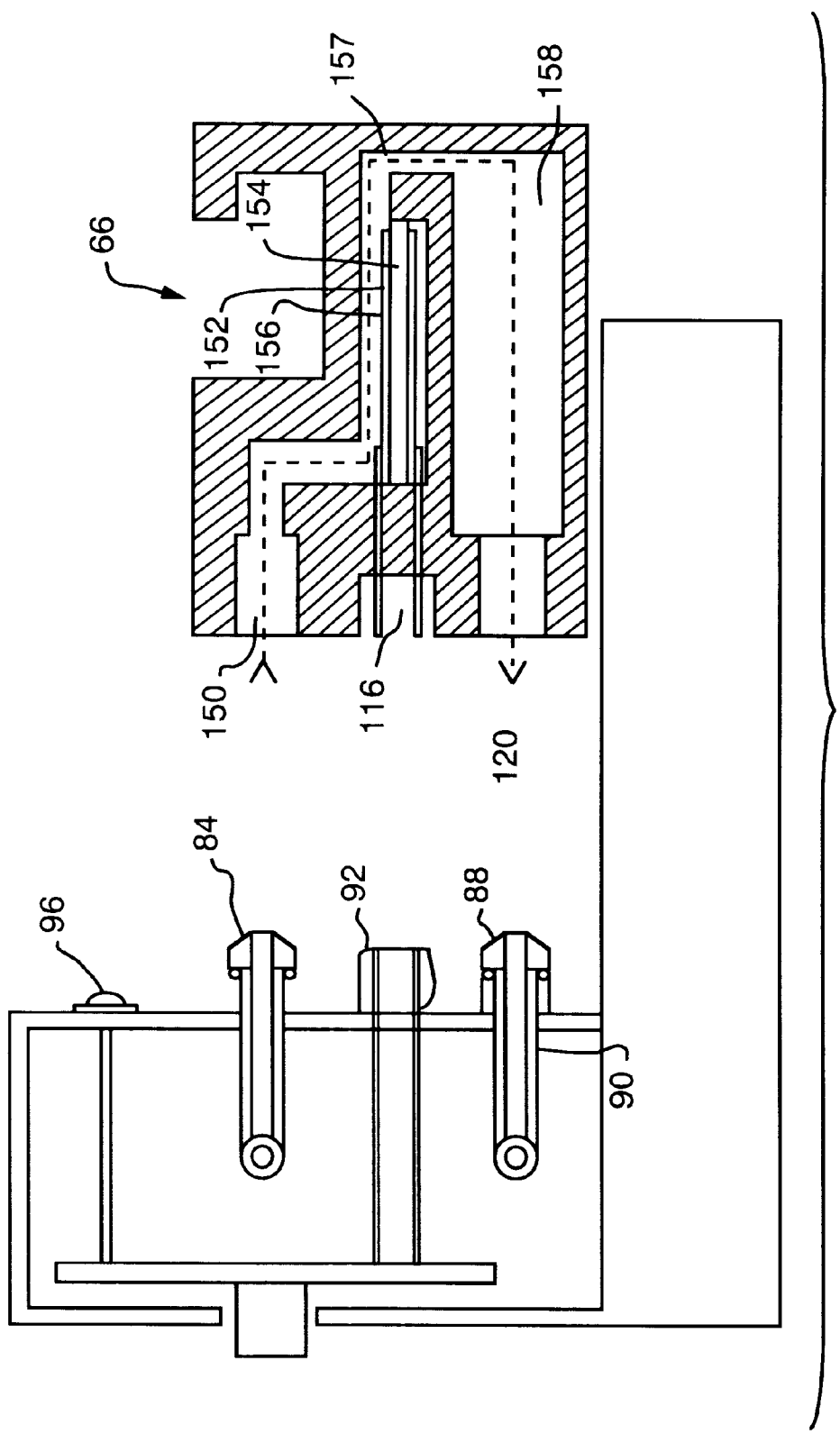
FIG. 7 is a cut side view of a second sensor cartridge, showing a water inlet and outlet and a resin incorporated BAW device.

The analyte water then passes through the first water outlet 78 and into the second sensor cartridge 66, shown in FIG. 7. The analyte water, shown in a flow path 120, enters the second sensor cartridge 66 through the water inlet recess 150, passes across a top surface 152 of a second BAW device 154, having a layer of ion exchange resin 156 doped with a marker ion, M, passes a water exit passage 157, and flows through a second bed of ion resin exchange resin 158, which is doped with the marker ion, M.

In these embodiments, the flow rate of the analyte water will be determined by a flow meter (not shown) with the rate in ml/sec being inputted to the microprocessor 20. It is preferred that the flow rate be less than 0.125 gpm and that the temperature range of the analyte water be between 45 and 75 degrees F. Thus, any type of flow meter capable of measuring fluids having these ranges of flow and temperature, and capable of sending a signal to the microprocessor, may be used. For example, magnetic flowmeters, coriolis mass flowmeters, vortex shedders, differential pressure meters or variable area flowmeters are all well known in the art and all may be adapted to measure the desired flows and produce the desired outputs.

The microprocessor converts the mass m, computed in Sauerbrey's equation to the number of ions of the target ions, T and T' by accessing a conversion table embedded in the microprocessor 20. The number of ions is adjusted by the capture ratio of the ion exchange resin. The microprocessor 20 then divides the number of ions accumulated in time t, and divides by the analyte water flow during time t. The result is the concentration of T and T' in the analyte. The concentration, in parts per billion, is transmitted to an output device, such as a PC, not shown. In the preferred embodiment, a microprocessor 20, such as the Motorola 68HC11, is be employed to perform frequency counting, linearization, computational functions, converting frequency to mass, table look-up functions including converting mass to number of ions and outputting MCL's for each ion being detected, arithmetic functions computing ppm (parts-per-million) or ppb (parts-per billion) and data conversion to output devices. However, in other embodiments a series of microprocessors adapted to perform different portions of the required calculations, and to provide the necessary outputs, may be used to achieve similar results.

As described above, the method of the present invention may be used to detect concentration levels of certain contaminants in an aqueous flow. However, the BAW system may be substituted for the conductivity system of the preferred embodiment to provide a failure detector for a filter cartridge. For example, if there was a need to detect Hg, Pb, and Ba, then detection of Cu, the ion that precedes those on the selectivity chart, would provide indication that the ion exchange resin was at a stage to break through for any of those elements. If the threshold ion is at the copper level, then when the ion exchange resin has reached a saturation stage in which copper is breaking through the resin, the filter cartridge needs replacement before heavier, more toxic metals elute into the filtered water. In this embodiment, the water passing from a water filter passes into a water inlet of a monitor base unit having a sensor cartridge. The sensor has a layer of ion exchange resin incorporated on a top electrode of the BAW device. The layer is doped with a marker ion, which in this case is calcium. Any ions having a selectivity coefficient higher than calcium will affix to the layer and displace calcium ions. Ions having selectivity coefficients lower than calcium will not affix to the resin layer. The exchange of heavier than calcium ions with calcium on the layer will increase the mass of the layer to the extent that heavier than calcium ions are present in the water less the mass of the calcium ions displaced. When a frequency drop of the BAW device indicates that the mass, m, of the layer has increased above a certain level, the microprocessor transmits an electronic output device, such as, a red light, which alerts the user that the water filter requires a change of the filtration cartridge.

In another embodiment for detecting and quantifying ions, the BAW device is replaced with the sensor substrate having conductive pads and the reference ions and target ions are detected and quantified by measuring changes in voltage rather than by changes in mass. This embodiment is identical to the monitors described with reference to FIGS. 1 and 2, except that a flowmeter and microprocessor are added to convert the changes in voltage into contamination levels, measured in parts per million, parts per billion, etc., of the desired contaminant.

In another embodiment of the invention, adapted for use on ultra-pure water lines, a cation resin having hydrogen on the exchange sites is disposed upon the ion collection portion. In this embodiment, the ultra-pure water flows across the resin and, if any cations are present, they displace the hydrogen on the resin. The resulting displacement may be detected and/or quantified utilizing either of the methods described above.

In another embodiment of the invention, adapted for use in connection with a nitrate-removing drinking water filter, an anion resin having chloride on the exchange sites is disposed upon the ion collection portion. In this embodiment, the collection portion is installed downstream of the filter and detects the breakthrough of nitrates through the filter by displacing the chlorides with nitrates on the collection portion. As was the case with the hydrogen ion embodiment above, the resulting displacement may be detected and/or quantified utilizing either of the methods described above.

In another embodiment, an ion selective polymer is employed in place of the calcium doped ion exchange resin to detect levels of copper. A polymer such as polyvinyl pyridine, PVP, is incorporated on a top electrode of a BAW device. Polyvinyl pyridine is selective for copper, i.e., if ions heavier or lower than PVP pass by a PVP incorporated layer, the ions will not affix to the surface. Thus, by measuring the mass loading of the PVP layer, the sensor containing the PVP layer will quantify the number of copper ions in the analyte. The embodiment can be used as a copper monitor, a threshold monitor for an ion exchange resin column or as a provider of $R_A$, the number of copper ions used as reference ions in an ion quantifying monitor.

In still other embodiments of the invention, other selective films are utilized in order to attract other contaminants, such as biological, inorganic and/or organic contaminants, in an aqueous stream. As was the case with the embodiments above, each may be readily adapted for use in a system for detecting the presence of the contaminant, for monitoring concentration levels of the contaminant, or for both detecting and quantifying the contaminant.

One group of selective films that may be utilized are molecularly imprinted polymers (MIP's). These polymers have a high selectivity for analyte molecules by having a complementary configuration to the target molecule. In this respect, they act like a synthetic antibody. In their paper titled *"Molecular Imprinting-Based Biomimetic Sensors Could Provide An Alternative To Often Unstable Biosensors For Industry, Medicine, And Environmental Analysis"*, Analytical Chemistry 1997, 69, 345A–349A (Jun. 1, 1997), incorporated herein by reference, Dario Kriz, Olof Ramström, and Klaus Mosbach of Lund University (Sweden) discuss the principles behind the use of MIP's with respect to sensor technology. By combining this MIP technology with the apparatus of the present invention, a wide range of biological and chemical substances may be detected and quantified.

In other embodiments of the invention, macrocyclic polimeric ethers (crown ethers) are utilized as selective films for attracting contaminants. Crown ethers are of specific interest due to their ability to form stable lipophilic complexes with metal cations and some organic compounds, and to transport ionic reagents from the aqueous into the organic phase.

A crown ether is a molecule containing hydrogen, carbon, and oxygen atoms. Each oxygen atom is bound between two of the carbon atoms and arranged in a ring (hence "crown"). When atoms of certain metallic elements pass through the center of the ring, they attach themselves to the exposed oxygen atoms and fit like a key in a lock. The crown compound then acts as "host," taking its "guest" to a place where it would not otherwise go—for instance, through the membrane that forms the wall of a cell. This high degree of selectivity enables the crown compound to "identify" the guest atom in a solution and wrap around it. In accepting specific atoms, lock-and-key fashion, crown ethers mimic the functions of biological materials such as enzymes.

In other embodiments of the invention, other selective films are utilized to detect and quantify biological or other organic contaminants. In some such embodiments, the selective film is an antibody film selective for a particular organic contaminant as its antigen. Examples of such antibody films are those selective for biological contamination, such as Giardia Lamblia and cryptosporidia, dioxin/furan antibodies for detecting the presence of dioxin/furan in the aqueous flow, and the like. In other such embodiments, a selective film of DNA strands, manufactured through a polymerase chain reaction (PCR), is utilized.

In still other embodiments, selective films of cyclodextrins (CD's) are utilized to attract certain organic molecules and inorganics. On its Internet Web Site at "http.//www.cyclodex.com", CTD, Inc. of Gainesville, Fla. describes the structure and selectivity of CD's as follows: "natural CDs are produced from starch by the action of cyclodextrin glycosyltransferase (CGTase), an enzyme produced by several organisms, Bacillus macerans being the most common. Structurally CDs consist of 6, 7, or 8 (a, b, and g respectively) D-glucopyranosyl units connected by alpha-(1,4) glycosidic linkages. The most stable three dimensional molecular configuration for these non-reducing cyclic oligosaccharides takes the form of a toroid with the upper (larger) and lower (smaller) opening of the toroid presenting secondary and primary hydroxyl groups, respectively, to the solvent environment. The interior of the toroid is hydrophobic as a result of the electron rich environment provided in large part by the glycosidic oxygen atoms. It is the interplay of atomic (Van der Waals), thermodynamic (hydrogen bonding), and solvent (hydrophobic) forces that accounts for the stable complexes that may be formed with chemical substances while in the apolar environment of the CD cavity. Once the molecule has entered the cavity, the "goodness of fit", as determined by the weak interactions taking place in the cavity, will make the final contribution to the association component of the equilibrium process. These weak forces can create selective interactions similar to those of enzymes." As set forth by CTD, Inc. on the above referenced Internet Web Site, a number of natural and synthetic CD's are commercially available, while others may be developed to capture other desired molecules.

Finally, other embodiments of the invention utilize cyclophanes to detect contaminants. The term "cyclophanes" applies to cyclic systems consisting of ring(s) or ring system (s) having the maximum number of noncumulative double bonds connected by saturated and/or unsaturated chains. Names for cyclophanes are formed by the operation of replacing a single atom of a cyclic parent "phane" structure by a cyclic structure." See. *IUPAC Commission on Nomen-* clature of Organic Chemistry: A Guide to IUPAC Nomenclature of Organic Compounds (Recommendations 1993), 1993, Blackwell Scientific Publications.

In each of the above referenced embodiments, the selective film is preferably deposited on a BAW device such that the presence of a particular contaminant in the aqueous flow is detected and quantified by the change in frequency of oscillation of the BAW device due to detectable mass loading on the BAW device.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. A method for detecting at least one contaminant in an aqueous flow comprising the steps of:

providing a conduit having at least one ion collection portion upon which is disposed a selective film such that said selective film is selective for said at least one contaminant;

disposing the aqueous flow through the conduit;

attracting at least one contaminant to said selective film; and detecting said at least one contaminant based upon a predetermined property of said contaminant disposed upon said selective film.

2. The method as claimed in claim 1 wherein said selective film comprises a molecularly imprinted polymer.

3. The method as claimed in claim 1 wherein said selective film comprises a crown ether.

4. The method as claimed in claim 1 wherein said selective film comprises an antibody film.

5. The method as claimed in claim 4 wherein said antibody film comprises biological antibodies for detecting biological contaminants.

6. The method as claimed in claim 5 wherein said biological contaminants are selected from a group consisting of Giardia Lamblia and cryptosporidia.

7. The method as claimed in claim 4 wherein said antibody film comprises dioxin antibodies for detecting a dioxin.

8. The method as claimed in claim 4 wherein said antibody film comprises furan antibodies for detecting a furan.

9. The method as claimed in claim 1 wherein said selective film comprises a cyclodextrin.

10. The method as claimed in claim 1 wherein said selective film comprises a cyclophane.

11. An apparatus for detecting at least one contaminant in an aqueous flow, said apparatus comprising:

a conduit;

a collection portion disposed within said conduit, said collection portion comprising a selective film such that said selective film is selective for said at least one contaminant;

a sensor for sensing a plurality of contaminants collected on said collection portion and sending a signal corresponding to a value of a predetermined property of said contaminants; and a microprocessor in communication with said sensor, said microprocessor being programmed to process said signal and determine the presence of at least one of said contaminants based upon the processed signal;

wherein the aqueous flow flows through said conduit, a plurality of contaminants are attracted to said selective film and are bonded to said selective film, said sensor senses the bonding of the contaminants to said selective film and sends to said microprocessor corresponding to the value of the predetermined property of the contaminants, and said microprocessor processes the signal and determines the presence of at least one of said contaminants based upon the processed signal.

12. The apparatus as claimed in claim 11 wherein said selective film comprises a molecularly imprinted polymer.

13. The apparatus as claimed in claim 11 wherein said selective film comprises a crown ether.

14. The apparatus as claimed in claim 11 wherein said selective film comprises an antibody film.

15. The apparatus as claimed in claim 14 wherein said antibody film comprises biological antibodies for detecting biological contaminants.

16. The apparatus as claimed in claim 15 wherein said biological contaminants are selected from a group consisting of Giardia Lamblia and cryptosporidia.

17. The apparatus as claimed in claim 14 wherein said antibody film comprises dioxin antibodies for detecting a dioxin.

18. The apparatus as claimed in claim 14 wherein said antibody film comprises furan antibodies for detecting a furan.

19. The apparatus as claimed in claim 11 wherein said selective film comprises a cyclodextrin.

20. The apparatus as claimed in claim 11 wherein said selective film comprises a cyclophane.

* * * * *